US008198586B2

(12) United States Patent
Moini

(10) Patent No.: US 8,198,586 B2
(45) Date of Patent: Jun. 12, 2012

(54) INTERFACING LOW-FLOW SEPARATION TECHNIQUES

(75) Inventor: Mehdi Moini, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 226 days.

(21) Appl. No.: 12/501,600

(22) Filed: Jul. 13, 2009

(65) Prior Publication Data
US 2010/0001181 A1 Jan. 7, 2010

Related U.S. Application Data

(63) Continuation of application No. PCT/US2008/051003, filed on Jan. 14, 2008.

(60) Provisional application No. 60/884,799, filed on Jan. 12, 2007.

(51) Int. Cl.
H01J 49/04 (2006.01)
B01D 59/44 (2006.01)
(52) U.S. Cl. ...................................................... 250/288
(58) Field of Classification Search .................... 250/288
See application file for complete search history.

(56) References Cited

U.S. PATENT DOCUMENTS

| 5,462,646 | A | 10/1995 | Shieh |
| 6,159,353 | A | 12/2000 | West et al. |
| 6,175,112 | B1 | 1/2001 | Karger et al. |
| 7,544,932 | B2 | 6/2009 | Janini et al. |
| 2004/0267459 | A1* | 12/2004 | van der Greef et al. ........ 702/30 |

FOREIGN PATENT DOCUMENTS

| WO | 2007/092227 A2 | 8/2007 |
| WO | 2008/089143 A1 | 7/2008 |

OTHER PUBLICATIONS

Bateman et al., Disposable Emitters for On-line Capillary Zone Electrophoresis/Nanoelectrospray Mass Spetrometry, 1997, Rapid Communications in Mass Spectrometry, vol. 11, pp. 307-315.*
Ettre, 'Nomenclature for Chromatography' 1993, Pure and Applied Chemistry, vol. 65, No. 4, pp. 823-872.*
International Search Report and Opinion (PCT/US2008/051003), Dated Apr. 16, 2008.
International Preliminary Report of Patentability (PCT/US2008/051003), Dated Jul. 14, 2009.
Supplemental European Search Report for EP 08 71 3753, dated Mar. 22, 2010.
Whitt et al., "Capillary Electrophoresis to Mass Spectrometry Interface Using a Porous Junction," Analytical Chemistry, Apr. 3, 2003, pp. 2188-2191, vol. 75, No. 9, American Chemical Society, US.

(Continued)

Primary Examiner — Jack Berman
Assistant Examiner — Eliza Osenbaugh-Stewart
(74) Attorney, Agent, or Firm — Baker Botts L.L.P.

(57) ABSTRACT

A capillary column, and method for forming a capillary column, in which the capillary column comprises at least one porous segment at a terminus of the capillary column, wherein the at least one porous segment is formed by exposing the segment to one or more of a solution of acid, base, and a mechanical tool.

20 Claims, 15 Drawing Sheets 250 nL/min flow
(magnified ~100x)

1000 nL/min flow
(magnified ~50x)

OTHER PUBLICATIONS

Xing-Zheng et al., "In-capillary Preconcentration of Proteins for Capillary Electrophoresis using a Cellulose Acetate-Coated Porous Joint," Analytical and Bioanalytical Chemistry, Jun. 1, 2005, pp. 848-852, vol. 382, No. 3, Springer, Berlin, DE.

Dolnik, "Capillary Electrophoresis of Proteins 2003-2005," Electrophoresis, Jan. 1, 2006, pp. 126-141, vol. 27, No. 1.

Wei, et al., "On-Line Concentration of Proteins and Peptides in Capillary Zone Electrophoresis with an Etched Porous Joint," Analytical Chemistry, Jun. 1, 2002, pp. 3899-3905, vol. 74.

Moini, "Simplifying CE-MS Operation. 2. Interfacing Low-Flow Separation Techniques to Mass Spectrometry Using a Porous Tip," Analytical Chemistry, Jun. 1, 2007, pp. 4241-4246, vol. 79. No. 11.

Garza, et al., "Simplifying Capillary Electrophoresis-Mass Spectrometry Operation: Eliminating Capillary Derivatization by Using Self-Coating Background Electrolytes," Journal of Chromatography A, Feb. 17, 2007, pp. 14-21, No. 1159.

Garza, et al., "Analysis of Complex Protein Mixtures with Improved Sequence Coverage Using (CD-MS/MS)n," Analytical Chemistry, Oct. 15, 2006, pp. 7309-7316, vol. 78, No. 20.

Nguyen, et al., "Analysis of Major Protein—Protein and Protein—Metal Complexes of Erythrocytes Directly from Cell Lysate Utilizing Capillary Electrophoresis Mass Spectrometry," Analytical Chemistry, Sep. 15, 2008, vol. 80, No. 18.

Moini, M., "Capillary electrophoresis mass spectrometry and its application to the analysis of biological mixtures," Anal. Bioanal. Chem. 2002, 373, 466-480.

Brocke, A. V., et al., "Recent advances in capillary electrophoresis/electrospray-mass spectrometry," Electrophoresis, 2001, 22, 1251-1266.

Cai, J., et al., "Capillary electrophoresis-mass spectrometry," J. of Chromatography, 1995, 703, 667-692.

Preisler, J., et al., "Capillary Electrophoresis-Matrix-Assisted Laser Desorption/Ionization Time-of-Flight Mass Spectrometry Using a Vacuum Deposition Interface," Anal. Chem., 2000, 72, 4785-4795.

Moini, M., "Design and Performance of a Universal Sheathless Capillary Electrophoresis to Mass Spectrometry Interface Using a Split-Flow Technique," Anal. Chem, 2001, 73, 3497-3501.

Figeys, D., et al., "Identification of proteins by capillary electrophoresis-tandem mass spectrometry: Evaluation of an on-line solid-phase extraction device," J. Chromatography A, 1997, 763, 295-306.

Quirino, J. P., et al., "Strategy for On-Line Preconcentration in Chromatographic Separations," Anal. Chem., 2001, 73, 5539-5543.

Quirino, J. P., et al., "On-Line Preconcentration in Capillary Electrochromatography Using a Porous Monolith Together with Solvent Gradient and Sample Stacking," Anal. Chem., 2001, 73, 5557-5563.

Khandurina, J., et al., "Microfabricated Porous Membrane Structure for Sample Concentration and Electrophoretic Analysis," Anal. Chem., 1999, 71 1815-1819.

Guzman, N.A., et al., "The use of selective adsorbents in capillary electrophoresis-mass spectrometry for analyte preconcentration and microreactions: A powerful three-dimensional tool for multiple chemical and biological applications," Electrophoresis, 2001, 22, 3602-3628.

Wei, W., et al., "One-Step Concentration of Analytes Based on Dynamic Change in pH in Capillary Zone Electrophoresis," Anal. Chem., 2002, 74, 932-940.

Figeys, D., et al., "High sensitivity analysis of proteins and peptides by capillary electrophoresis-tandem mass spectrometry: Recent developments in technology and applications," Electrophoresis, 1998, 19, 885-892.

Wei, W., et al., "On-Line Concentration of Proteins and Peptides in Capillary Zone Electrophoresis with an Etched Porous Joint," Anal. Chem., 2002, 74, 3899-3905.

Krylov, S., et al., "Capillary Electrophoresis for the Analysis of Biopolymers," Anal. Chem., 2000, 71, 111R-128R.

* cited by examiner

Figure 3
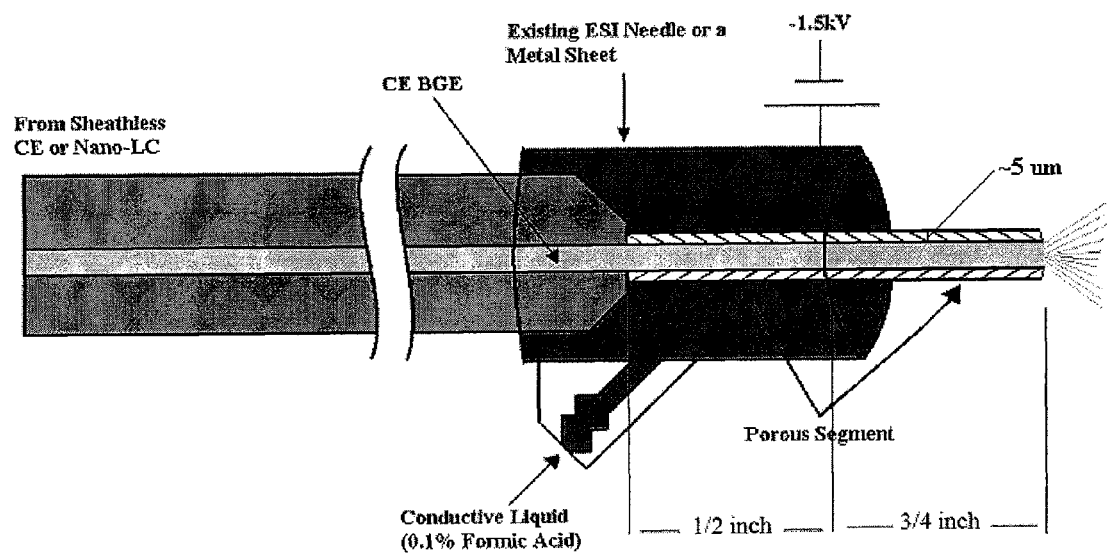
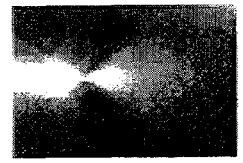
250 nL/min flow
(magnified ~100x)
1000 nL/min flow
(magnified ~50x)

Figure 11
Polybrene
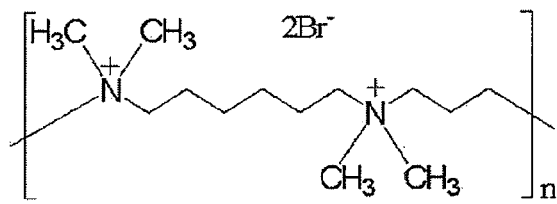
PolyE_323
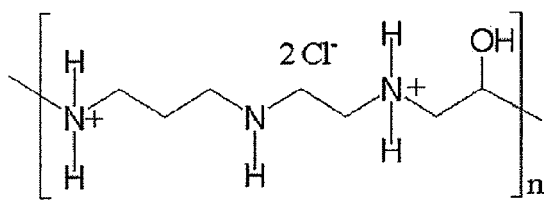
Figure 12
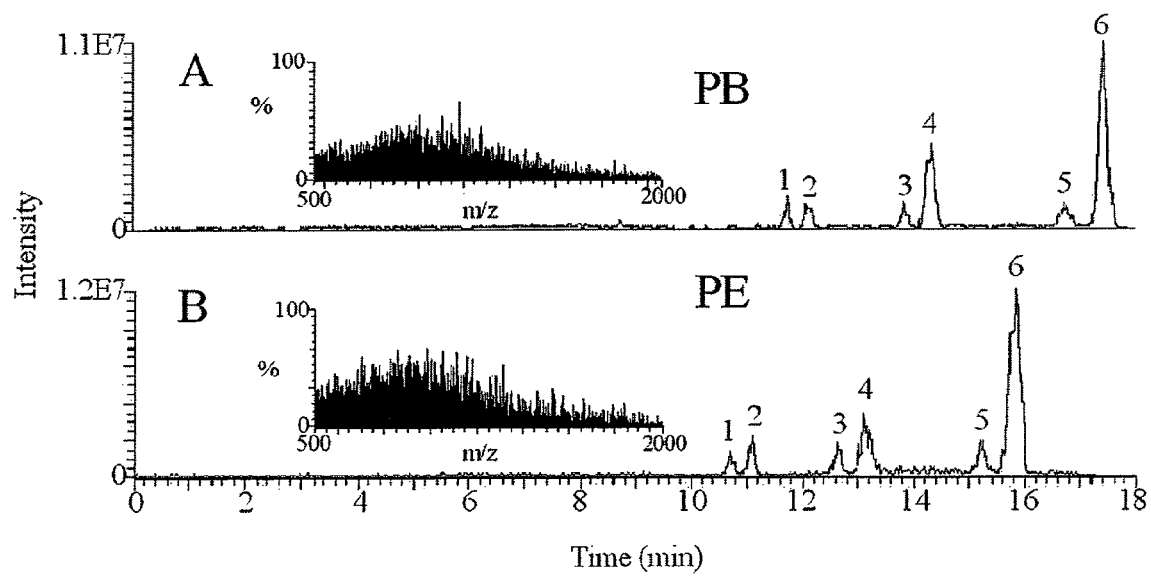

HPLC to MS interface

INTERFACING LOW-FLOW SEPARATION TECHNIQUES

CROSS REFERENCE TO RELATED APPLICATIONS

This application is a continuation of International Patent Application No. PCT/US2008/051003 filed Jan. 14, 2008, which claims the benefit of U.S. Provisional Application No. 60/884,799 filed Jan. 12, 2007, both of which are incorporated by reference.

BACKGROUND

Analysis of a large number of complex samples at low quantity and limited sample volume requires an analytical technique with fast analysis time, high specificity, high sensitivity, and high resolution. To achieve high resolution and high sensitivity under electrospray ionization (ESI) technique, separation techniques that use narrower columns/capillaries with low flow rates, such as nano-liquid chromatography (nano-LC) and capillary electrophoresis (CE), have become wide spread. For example, in high performance liquid chromatography-mass spectrometry (HPLC-MS), 75-μm-i.d. reverse phase columns with flow rates of ~250 mL/min (nano-LC) have become the column of choice for proteomics study. In nano-liquid chromatography-mass spectrometry (nLC-MS), as long as the flow rates in the analytical capillaries are >100 mL/min, electrical connection to the end of these capillaries for electrospray ionization is usually achieved through a "zero dead volume" union/Tee.

In conventional capillary electrophoresis mass spectrometry (CE-MS), where a 50 or 75-μm-i.d. capillary is usually used, sheath-flow interfaces that provide voltage to the capillary outlet through addition of conductive liquid are utilized. To achieve higher resolution and more sensitivity, even narrower columns with lower flow rates such as nLC-MS using column diameter of less than 75-μm, or alternatively CE-MS with narrower capillaries (<30-μm-i.d.) with flow rates in the low nL/min are gaining popularity [1]. At these low flow rates however, conventional interfacing techniques, such as attaching a nano-spray tip to the analytical capillary using a union, are no longer useful because of the dead volume that they introduce in the interface region.

Over the years, three general techniques have been developed to address the need for interfacing narrow capillaries with low flow rates to MS via ESI: sheath-flow, sheathless, and split-flow interfaces [2-11]. Sheath-flow techniques bear several disadvantages: (1) dilution of the analyte by the sheath liquid; (2) competition for available charge between the species present in the sheath-flow and the analyte in the ESI process (Gale and Smith 1993); and (3) effects on separation, solubility, or molecular conformation which vary according to sheath liquid composition (Thompson et al. 1993, Foret et al. 1994, Smith et al. 1991). Therefore, in recent years, sheathless and split-flow interfaces have become more popular for interfacing low flow rates capillaries to MS because of their higher sensitivity of detection, which results from the absence of a sheath liquid to dilute the capillary effluent.

In split-flow techniques, a small portion of the capillary flow is diverted outside of the capillary through a small hole near the capillary outlet [12]. However, when applied to capillaries with i.d. <30-μm, controlling the split ratio using mechanical tools was difficult. This disadvantage was eliminated with a porous junction design [2], in which an electrical connection to the CE capillary outlet was achieved by making a small section of the capillary near the outlet porous. After sharpening the capillary outlet tip, the porous junction was inserted into the existing ESI needle (or sheath metal tubing) filled with a conductive solution (background electrolyte-BGE). Application of high voltage to the sheath metal containing BGE causes oxidation (in positive mode) or reduction (in negative mode) of water (if aqueous solution was used as the BGE). Ion-transport through the porous junction closes the CE circuit and provides voltage for ESI. In this design it is ion and not liquid transport through the porous section that provides electrical connection to the capillary outlet.

The use of ion transport through a porous section of a capillary for closing the electrical circuit has been employed before including: (1) a nanospray tip attached to the CE capillary outlet using polysulphone microdialysis tubing [13], (2) a liquid junction through a porous segment around the entire circumference of the capillary near the outlet [14], and (3) through a porous glass joint [15]. However, the major disadvantage of attaching a nanospray tip to the capillary outlet using polysulphone microdialysis tubing is that because the capillary inner diameter is usually smaller than the wall thickness, there is a relatively large dead volume where the two capillaries are joined. The draw back of employing a liquid junction for making the electrical connection is that since the entire circumference of the capillary was etched till porous, the porous section of the capillary is very weak and requires a liquid junction to hold the two segments of the capillary (before and after the porous section) together.

Making a section of a capillary porous has also been used in CE for other purposes than CE-to-MS interfacing. For example, porous capillary at the inlet end was recently used for the on-line concentration of proteins and peptides in capillary electrophoresis in which a short length along the capillary (around the entire circumference of the capillary) was etched with HF [16]. In CE with electrochemical detection, porous CE capillaries have been used to isolate the electrochemical detector from the CE electrical field [17-21]. In our previously reported porous junction design [2], because only a very small section of the circumference of the capillary is made porous, the capillary maintains its integrity. In addition, the inner wall of the capillary remains intact and therefore, no dead volume was introduced into the capillary. Moreover, since no liquid is added to the capillary outlet, the porous junction design provided high sensitivity. However, there were two disadvantages with the porous junction design. Because mechanical tools are used to make the well to produce porous junction, fabrication of the interface on a reproducible and large scale is impractical. In addition, the capillary outlet has to be sharpened in a separate process. Furthermore, lack of an automated, robust, and reproducible method for interfacing narrow capillary with low flow rates to MS has, for example, prevented CE-MS to become a widespread separation technique.

SUMMARY

The present disclosure provides, among other things, approaches for interfacing low flow separation techniques, such as capillary electrophoresis and nano HPLC to mass spectrometry via electrospray ionization [22]. More particularly, it concerns capillary columns having a porous segment, or porous tip, useful for interfacing low flow separation techniques, as well as methods and systems using such capillary columns.

The design of the porous tip of the present disclosure has several advantages over previous designs. First, production may be automated and the mass produced in a reproducible manner. Another advantage is that several capillary outlets may be etched at about the same time in ~30 min (for 150-μm-o.d. and 20 μm-i.d. capillaries). Additionally, the interface may be used for both nano-LC-MS and CE-MS. Furthermore, the etching process sharpens the tip and makes the capillary porous in one step, thus eliminating the separate tip sharpening process of previous designs. Finally, because of the long length of the porous section (~1 inch), if the outlet tip is blocked or damaged, a small section (~1 mm) of it may be cut or etched away using HF without any loss of the interface performance, thus extending its useful life. Because a longer section of the porous tip (~0.5-1 inch) has the same wall thickness (FIG. 1) removing a small section (~1 mm each time for a total of say ~1 cm) of it does not affect its performance. In addition to these advantages, the inner wall of the capillary remains intact and there is no dead volume associated with the porous tip design. This ensures the best resolution from the CE separation whereas most designs have dead volume which leads to peak broadening. Moreover, because the actual metal/liquid contact occurs outside of the capillary, bubble formation due to redox reactions of water at the high voltage electrode does not affect separation or MS performance. Because the tip of the porous tip design is glass, there is no reason for the porous tip to increase the risk of arcing, which could reduce capillary durability. The performance of this interface is demonstrated by the analyses of amino acids, peptide, and protein mixtures.

While the present disclosure is susceptible to various modifications and alternative forms, specific example embodiments have been shown in the drawings and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DRAWINGS

Some specific example embodiments of the disclosure may be understood by referring, in part, to the following description and the accompanying drawings.

FIG. 3 is a schematic of the porous tip.

FIG. 11 is the molecular structures of polyE__323 (PE) and polybrene (PB).

FIG. 12 is a comparison of 33 nM PB in 0.1% acetic acid (A) and 33 nM PE in 0.1% acetic acid (B) as the self-coating BGE for the CE-MS analysis of the 6 intact protein mixture containing: (1) β-lactoglobin (bovine), (2) myoglobin (horse), (3) hemoglobin-α (human), (4) hemoglobin-β (human), (5) lysozyme (chicken), and (6) cytochrome c (horse). The insets show the average (over one minute) background mass spectra of Panel A and B.

Figure 13:
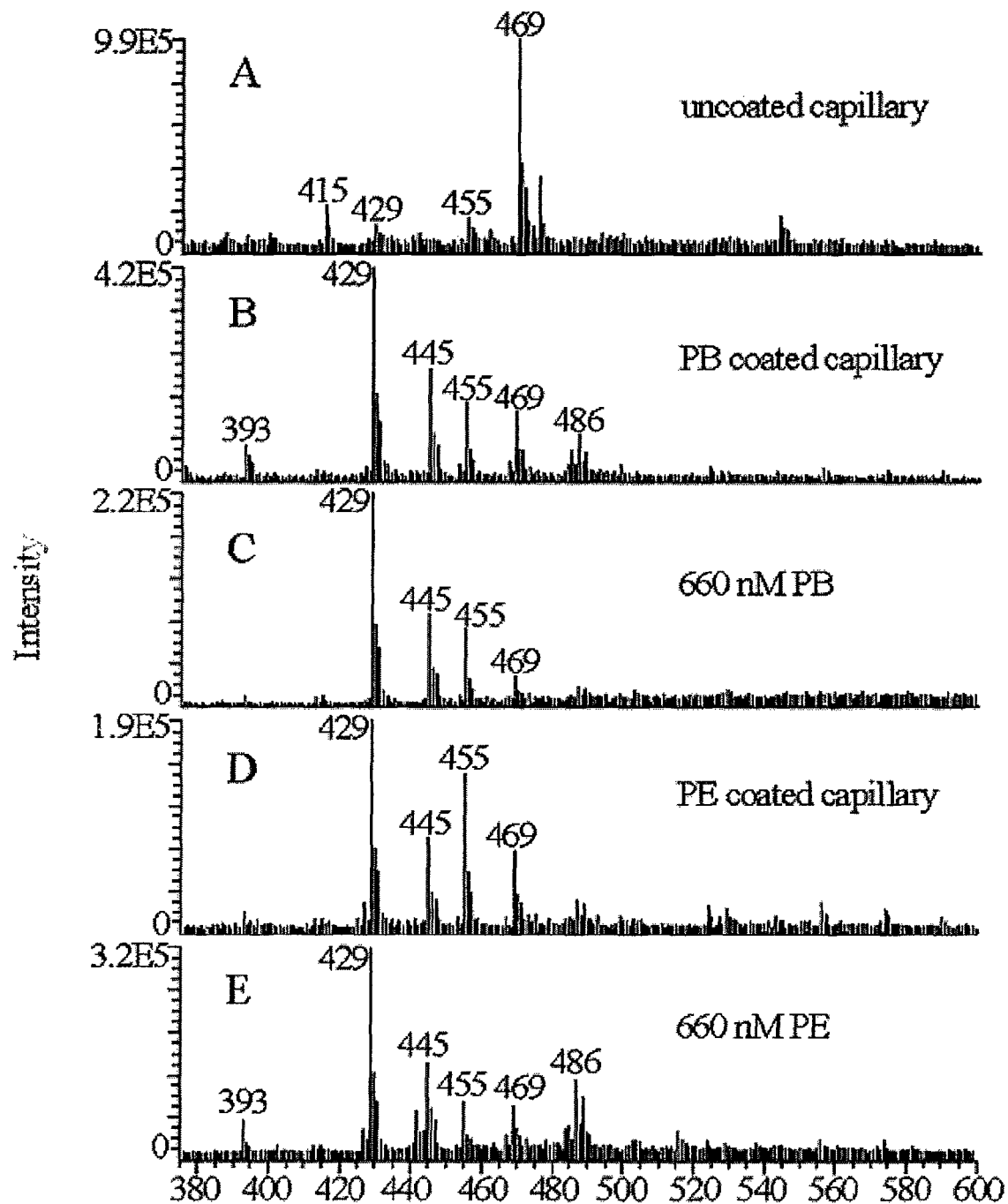

FIG. 13 is the average background mass spectra (from 2-3 minutes) of the electropherograms from FIG. 3 using (A) 0.1% acetic acid BGE in an uncoated capillary, (B) 0.1% acetic acid in a PB pre-coated capillary, (C) 660 fmol PB additive in 0.1% acetic acid in an uncoated capillary, (D) 0.1% acetic acid in a PE pre-coated capillary. (E) 660 fmol PE additive in 0.1% acetic acid in an uncoated capillary.

Figure 14:
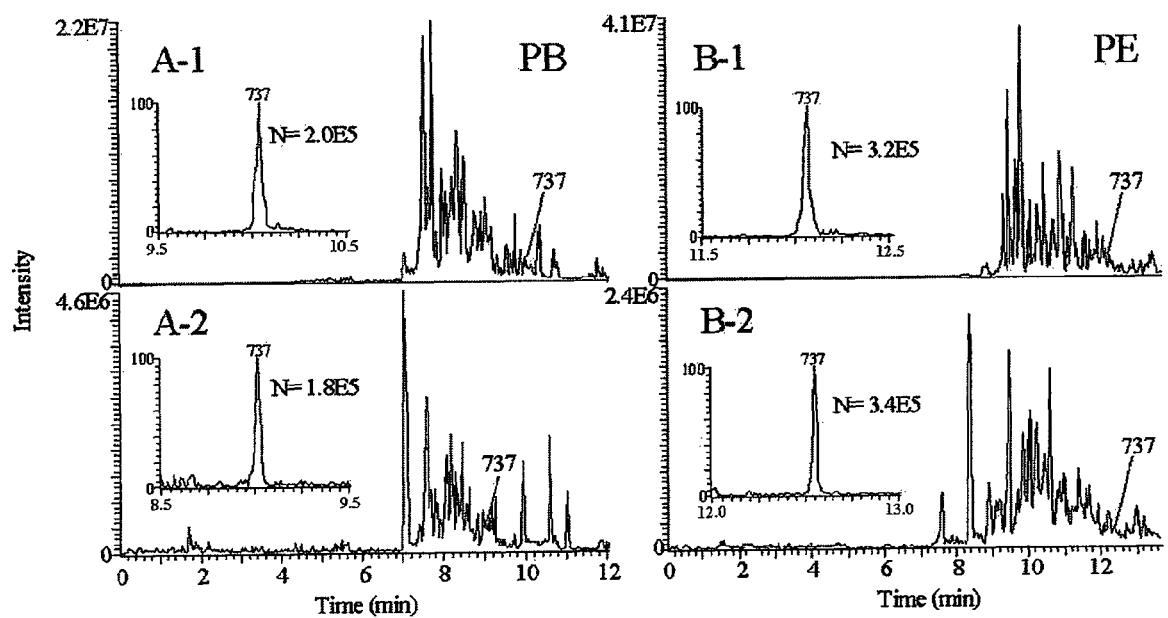

FIG. 14 is a comparison of the CE-MS analyses of the stock solution of the six protein digest using the 33 nM PB (Panel A1) and PE (Panel B1), and the 10× diluted protein digest (Panels A2 and B2). The insets show the ion electropherograms of m/z 737 (protonated KEFGVER from rat phosphorylase b) for these Panels and the separation efficiencies of this peak under the 4 different experimental conditions.

Figure 15:
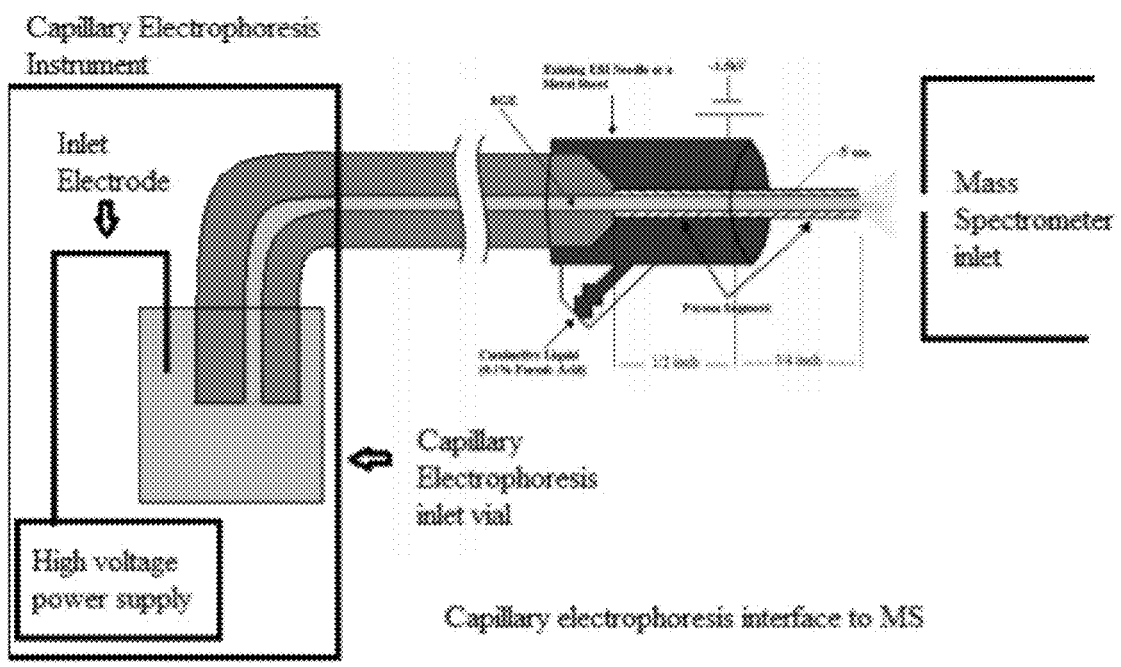

FIG. 15 is a schematic representation of a capillary column interfaced with an electrophoresis instrument and a mass spectrometry instrument.

Figure 16:
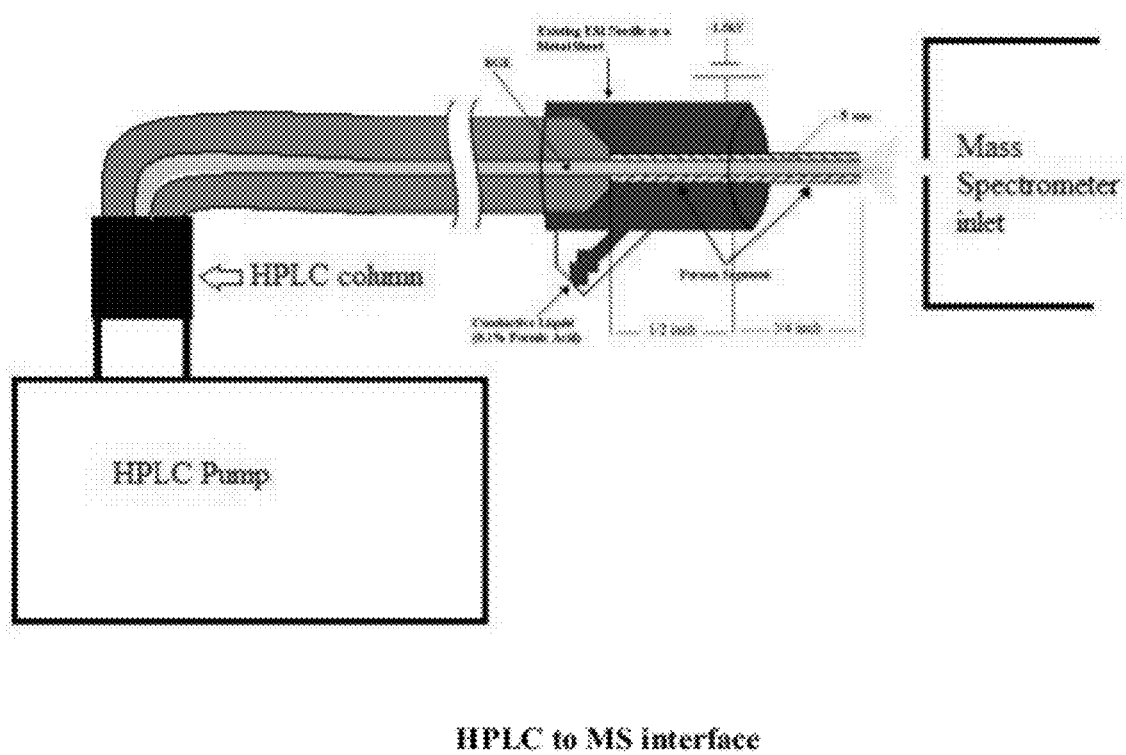

FIG. 16 is a schematic representation of a capillary column interfaced with a high performance liquid chromatography instrument and a mass spectrometry instrument.

Figure 17:
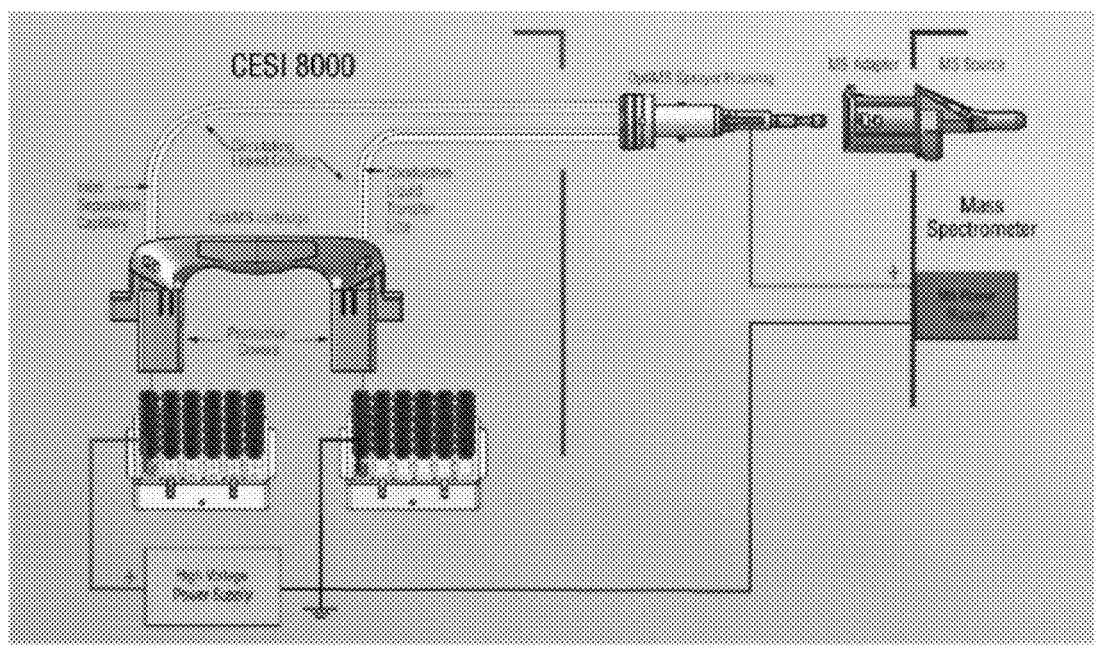

FIG. 17 is a schematic representation of a capillary column interfaced with an electrophoresis instrument and a mass spectrometry instrument.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as illustrated, in part, by the appended claims.

DESCRIPTION

The present disclosure provides, among other things, approaches for interfacing low flow separation techniques, such as capillary electrophoresis and nano HPLC to mass spectrometry via electrospray ionization. More particularly, it concerns capillary columns having a porous segment, or porous tip, useful for interfacing low flow separation techniques, as well as methods and systems using such capillary columns.

The present disclosure also provides capillary columns comprising at least one porous segment at a terminus of the capillary column, wherein the at least one porous segment is formed by exposing the segment to one or more of a solution of acid, base, and a mechanical tool. Such capillary columns (having a porous tip) may be used to interface low flow separation techniques by providing an electrical connection to the capillary outlet. The capillary columns of the present disclosure may be used to in, for example, separation techniques that use electron spray ionization (ESI), capillary electrophoresis, high performance liquid chromatography (HPLC), nano-LC, and mass spectrometry (MS). Additionally, the capillary columns of the present disclosure may be used as a nanospray tip which may be filled with analyte for long infusion. More than one porous segment may be installed on a capillary. For example, a second porous segment may be made at an inlet for sample concentration, or another one in the center to dynamically change the voltage in the capillary, as shown by our previous publication [23].

The present disclosure also provides methods for forming a porous segment, or tip, comprising providing a capillary column comprising a wall and a segment at a terminus of the capillary column and creating a porous segment at the terminus of the capillary column. Generally, the porous section is created by etching the tip using an acid or base solution or mechanical tools until it is porous. When using an acid or base solution, etching time may be dependent upon the concentration of the acid or base solution. For example, higher concentrations correspond to lower etching times and vice versa. In some instances, the capillary column wall comprises a polymer coating such as polyimide, which may be at least partially removed before etching the tip.

In one embodiment, the capillary is made by removing ~1 inch polyimide coating of the capillary outlet and etching it by immersing it into a solution of 49% HF until it is porous. For a given capillary o.d. and i.d., the etching time is constant, so long as a fresh HF solution is used each time. For example, the etching time is ~30 min for a capillary with 150-μm-o.d. and 20-μm-i.d. In some instances, only a portion of the tip may be etched. The methods of the present disclosure may be used to produce several capillary at the same time. The etching process also sharpens the tip of the capillary outlet for stable electrospray ionization. The electrical connection is achieved simply by inserting the capillary outlet containing the porous tip into the existing ESI needle (sheath metal) and filling the needle with a conductive solution (background electrolyte-BGE).

The ESI needle may be made of any conductive metal, such as stainless steel, platinum, gold, etc., or it may be a nonconductive tube with a metal connection such that voltage is applied to the BGE. Suitable examples of BGE include, but are not limited to, water, acid, or base solution, such as 0.1% acetic or formic acid or ammonium acetate solution. pH and concentration of BGE can affect EOF, however, pressure assisted CE can be used to modify BGE flow rate in the CE capillary without any significant loss of separation efficiency. Additives may also be included in the BGE, such as polybrene or Poly 323. Electrochemical (redox) reactions at the sheath metal and transfer of small ions through the porous tip into the capillary provide the electrical connection for the ESI and for the CE outlet electrode. The design is suitable for interfacing all capillary sizes with a wide range of flow rates to MS via ESI, however, it is especially useful for interfacing narrow (30-μm<i.d.) capillaries and low flow rates (<100 mL/min) such as those used in nano-liquid chromatography-mass spectrometry (nLC-MS) or capillary electrophoresis (CE-MS). CE flow rates for CE-MS are usually in the range of ~1-100 mL/min. Spray stability depends on the inner diameter and wall thickness of the CE-outlet/ESI tip. Lower flow rates require narrower capillaries and sharper tips. For example, ~10-μm-i.d. CE capillaries are used for flow rates below ~10 mL/min, etc.

According to certain embodiments, the present disclosure provides systems comprising a capillary column comprising a wall and at least one porous segment at a terminus of the capillary column, wherein the at least one porous segment is formed by exposing the segment to one or more of a solution of acid, base, and a mechanical tool; and one or more instruments chosen from an electrophoresis instrument, a high performance liquid chromatography instrument, and a mass spectrometry instrument, wherein the porous segment serves as the interface between the capillary column and the instrument.

According to certain embodiments, the present disclosure provides methods for chemically analyzing a chemical or biological sample comprising providing a capillary column having a wall and at least one porous segment at a terminus of the capillary column; providing a mass spectrometer in operable relation to the capillary column; interfacing the mass spectrometer with the at least one porous segment at a terminus of the capillary column; injecting a mixture containing the chemical or biological sample into the capillary column; transporting at least a portion of the mixture to the mass spectrometer; and analyzing the portion with the mass spectrometer to identify the composition of the chemical or biological sample in the portion. Yet another application of the porous tip is its use in conjunction with Matrix Assisted Laser Desorption Ionization (MALDI). In this case the outlet of the capillary is grounded through the porous tip, and CE eluents are deposited onto a MALDI plate for MS analysis.

To facilitate a better understanding of the present invention, the following examples of specific embodiments are given. In no way should the following examples be read to limit or define the entire scope of the invention.

EXAMPLES

Materials & Equipment

High performance liquid chromatography (HPLC) grade water and 49% HF are commercially available from Fischer Scientific, Pittsburgh, Pa. All other chemicals used are commercially available from Sigma Chemical Co., St. Louis, Mo. The Sigma HPLC peptide standard contains five peptides: GY (MW238), VYV (MW 379), YGGFL (leucine-enkaphalin, MW 555), YGGFM (methionine-enkaphalin, MW 573), and DRVYIHPF (angiotensin II, MW 1046). The contents of the vial (0.5 mg of each peptide) was dissolved in 1 mL of HPLC-grade water (Fischer). A 5× dilution of a 17-amino acid standard (2.5 μmoles/mL in 0.1 N HCl, except L-cystine at 1.25 μmoles/mL) was used, in the amino acid standard test. The protein standard contained a 10× dilution of the following proteins: hemoglobin A (MW 64,000), trypsinogen (MW 24,000), carbonic anhydrase (MW 29,000), and cytochrome c (MW 12,360). Each was tested under a 10× dilution. The protein digest contained: hemoglobin A (MW 64,000), trypsinogen (MW 24,000), carbonic anhydrase (MW 29,000), cytochrome c (MW 12,360), α-casein (MW 23,000), and β-casein (MW 24,000). They were digested according to the method published by Takada [24].

A P/ACE system MDQ CE instrument (Beckman-Coulter Instruments, Fullerton, Calif.) was used in conjunction with a Finnigan LCQ MS (Finnigan, San Jose, Calif.). The mass spectrometer was scanned in the mass/charge (m/z) range of 375-600 for the analysis of the peptide standard, 515-700 for the AAI18-C-6-TCA complex, 700-2000 for the protein standard, and 500-1500 for the complex protein digest.

For the analyses of the peptide mixture, the protein digest, and the protein mixture, the CE inlet electrode was −30 kV (reverse polarity mode), and the ESI voltage of was ~1.4 kV. A solution of 0.1% polybrene in 0.1% acetic acid is used as the background electrolyte. For the analysis of the amino acid mixtures, the CE inlet electrode was maintained at −20 kV. A solution of 15 mM 18-crown-6-tetracarboxylic acid (in 1 M formic acid) was used as the complexation reagent to enhance the sensitivity of detection of amino acids [25].

Different 20-μm-i.d. and 150-μm-o.d, fused-silica capillaries (Polymicro Technologies, Phoenix, Ariz.), varying in length from 60 cm-120 cm, were used throughout the experiment. The outlet of the capillary was made porous and sharp using 49% HF as $N_2$ gas was passed through it to minimize inner wall etching. The HF on the capillary wall was neutralized by a saturated solution of ammonium bicarbonate by successively immersing the outlet (etched section) of the capillary first into the ammonium bicarbonate solution and then into distilled water (both under the hood). The capillaries were then removed from under the hood and rinsed with distilled water off the tap. Nitrile gloves were worn during the process and disposed after each use.

Fabrication of Porous Tip Design

Figure 1:
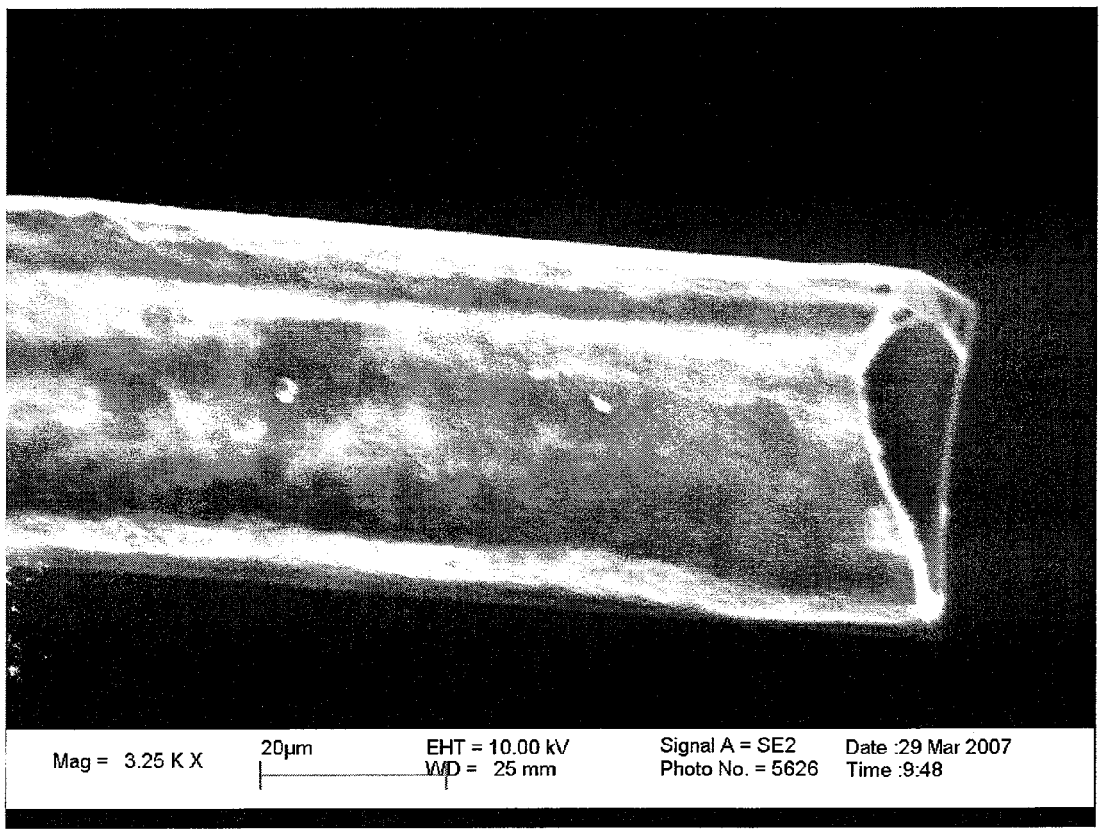
FIG. 1 is an electron micrograph of a porous tip capillary using scanning electron microscopy.
Figure 2:
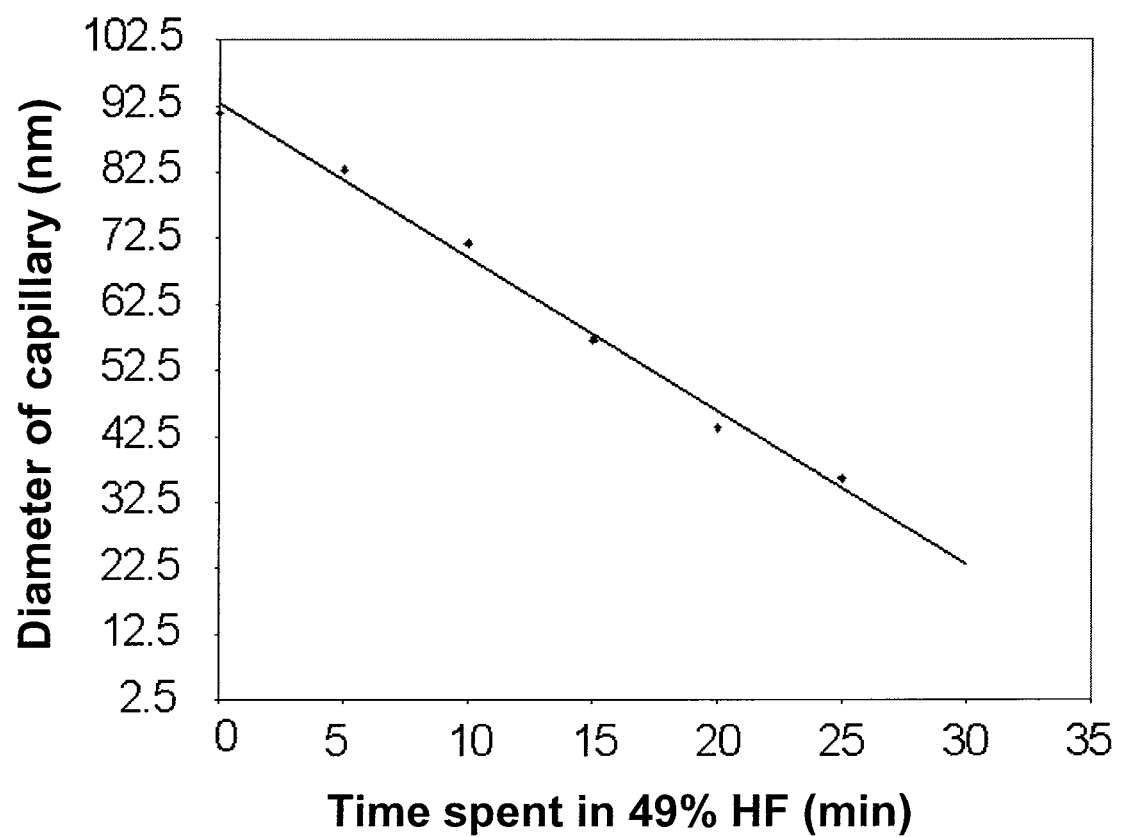
FIG. 2 is a graph of the average etching rate of 20-μm-i.d. capillaries, etched in fresh 49% HF solution.

In a first reduction to practice of the present invention, two capillaries were made porous at the same time. The fabrication procedure was as follows. Before etching the capillary outlets by HF solution, ~1 inch of the polyimide coating of the capillary outlets was removed using a flame. Other methods of removing polyimide coating, such as using sulfuric acid, also may be used. The exposed fused silica sections of the capillaries were then immersed into a Teflon container containing fresh HF solution. Nitrogen gas was introduced into the capillaries to prevent etching of the capillary inner walls during the etching process. The Teflon container was positioned inside a well-ventilated hood. For each capillary o.d. and i.d, the etching time was experimentally determined by first measuring the etching rate of the fused-silica in fresh HF solution. This was achieved by measuring capillary o.d. after successive etching time intervals (every ~5 min), and testing the capillary outlet for porosity. The porosity was checked by installing the capillary tip into an electrospray apparatus on the bench and testing the porous tip for EST. If the 0.1% solution of acetic acid exiting the capillary sprayed at less than 2 kV, the tip was porous. It was found that the fused silica material etched at an average rate of ~1.8 μm/min (FIG. 2). The capillaries become porous when the thickness of the wall of the capillary approached ~5 μm. For example, a nominal 150-μm-o.d., 20-μm-i.d. capillary becomes porous in ~28.5 minutes in 49% fresh HF solution [.~150-20 (for polyimid coating)=130-20 (for i.d.)=~110/2=55=wall thickness]. Because of its short etching time, and its good thermal conductivity, 150-μm-o.d, are the capillary of choice for CE-MS analysis, it was used in this study. However, other capillary outer and inner diameters also are utilized. For example, a 360-μm-o.d. capillaries provide better mechanical durability, however, ~82 minutes of etching time is required for a 30-μm-i.d. capillary. FIG. 3 shows the overall schematic of a porous tip design.

Performance Results

Figure 4:
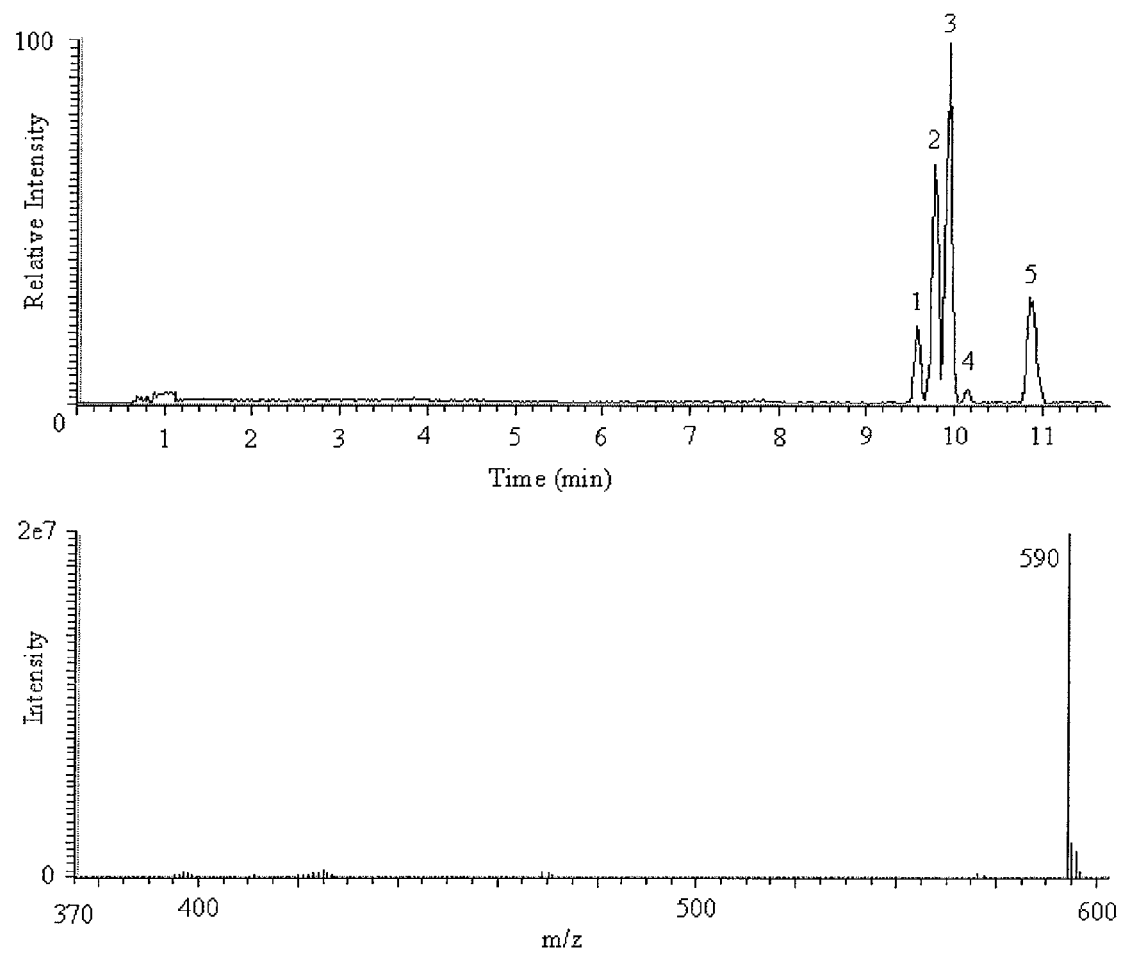
FIG. 4 (top) is a base peak chromatogram of the peptide standard (110 cm long capillary): 1) Oxidized-YGGFM, 2) YGGFM, 3) YGGFL, 4) VYV, 5) DRVYIHPF and (bottom) a mass spectrum of peak 1 in FIG. 4 (top).

Based on previous CE-MS studies, the Sigma HPLC peptide mixture is a suitable standard for testing the overall CE-ESI-MS performance. Baseline separation of the components of the test mixture is indicative of adequate performance of the capillary for the analysis of different mixtures. FIG. 4 shows the base peak electropherogram of the peptide standard. In the analysis of peptide standard, GY was not detected in the scanned mass range, angiotensin II was seen as a doubly charged compound (m/z 524), and methionine-enkaphalin was seen in the oxidized state (m/z 590). As shown, the full width at half maximum (FWHM) of most peptides are ~5 s.

Figure 5:
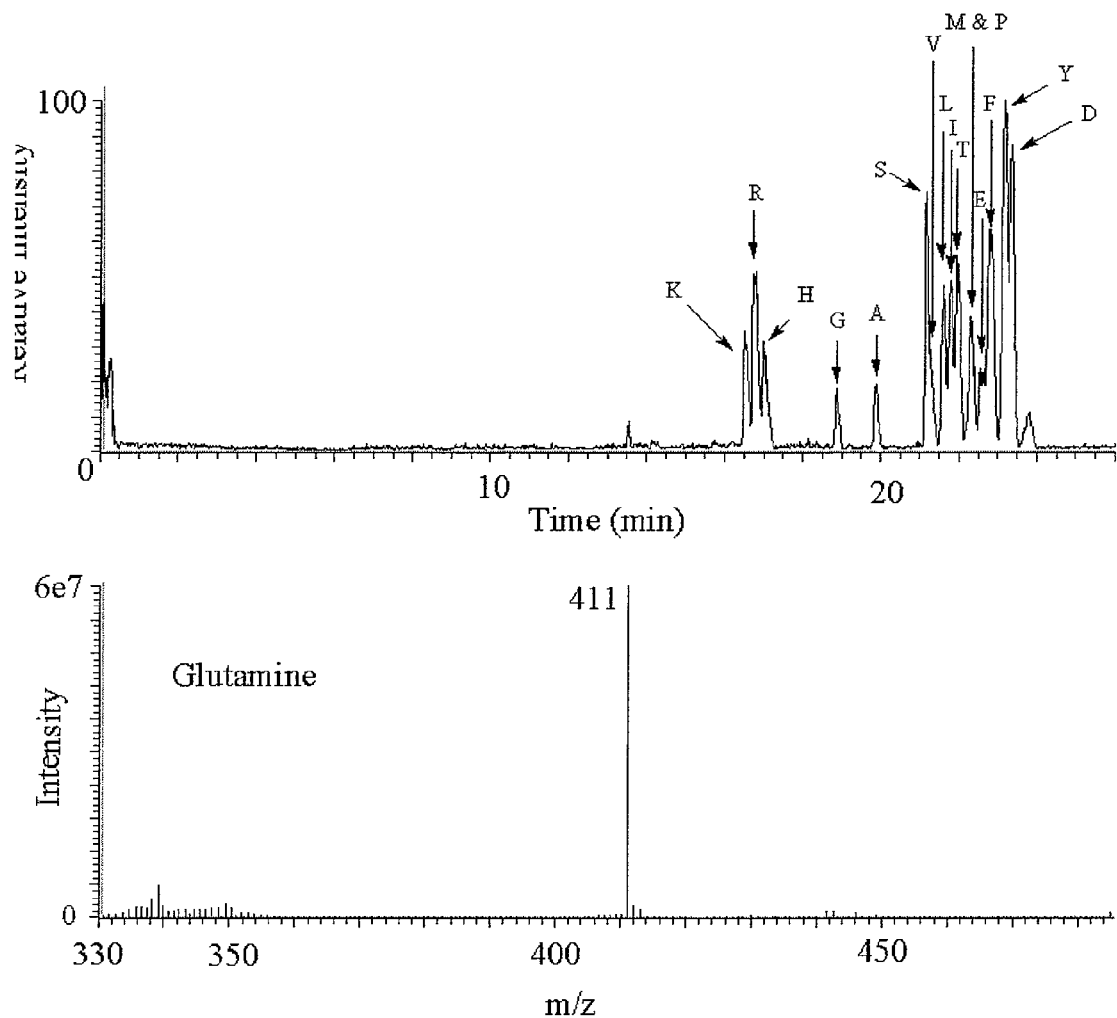
FIG. 5 (top) is a base peak electropherogram of 17 amino acid standard and (bottom) a mass spectrum of the peak representing glutamine-crown ether complex.

To test the utility of the porous tip for the analysis of amino acids, in which a 1 M solution of formic acid is the main ingredient of the BGE, CE-MS of an amino acid standard containing 17 amino acids was analyzed. FIG. 5 shows the base peak electropherogram of the 17 amino acid standards. Cysteine was the only amino acid not observed in the chromatogram, with methionine and proline co-migrating. Cysteine usually comes off as a dimer, which when complexed with 18-C-6 falls out of the scanned mass range. As shown, baseline separation of amino acids was observed, indicating the viability of porous tip for the analysis of small molecules such as amino acids [25].

Figure 6:
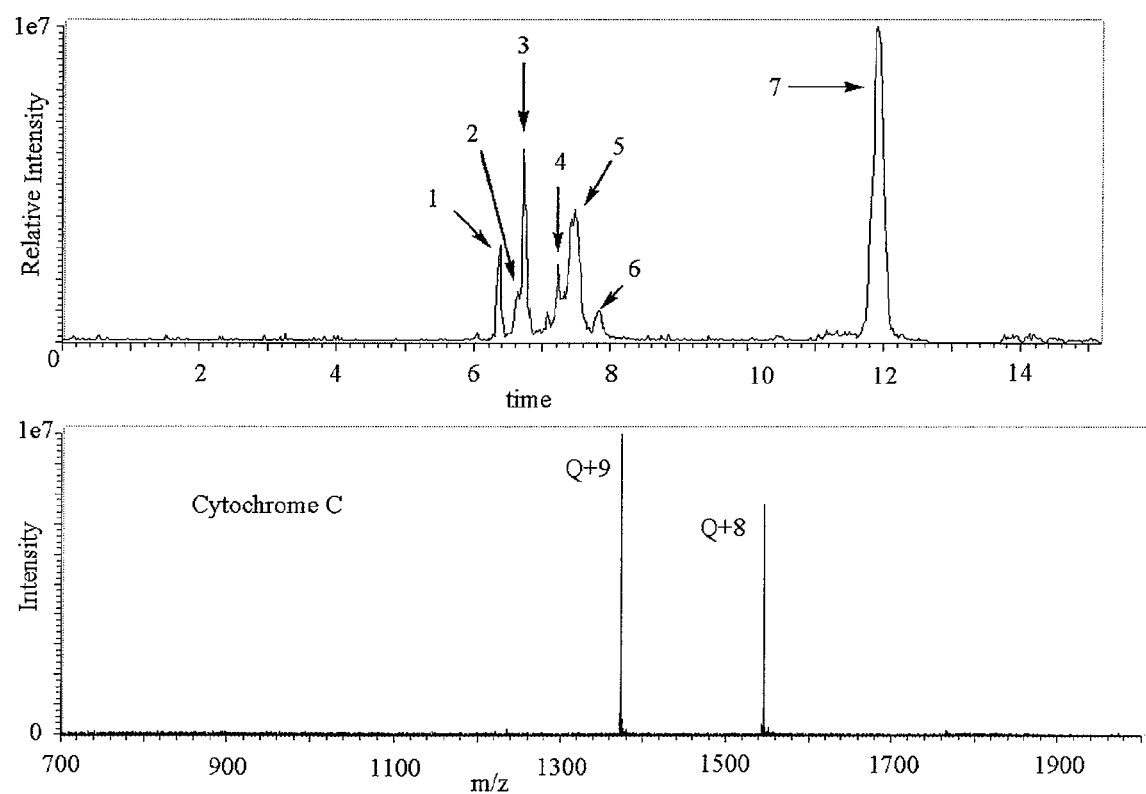
FIG. 6 is a base peak acetropherogram of the 6 protein standard (top): 1) Protein fragment peak, 8,297MW, 2) Hem-A-0-subunit, 3) Protein fragment peak, 8,562MW, 4) Trypsinogen, 5) Carbonic anhydrase, 6) Hem-A α-subunit, and 7) Mass spectrum of cytoclarome c (bottom).
Figure 7:
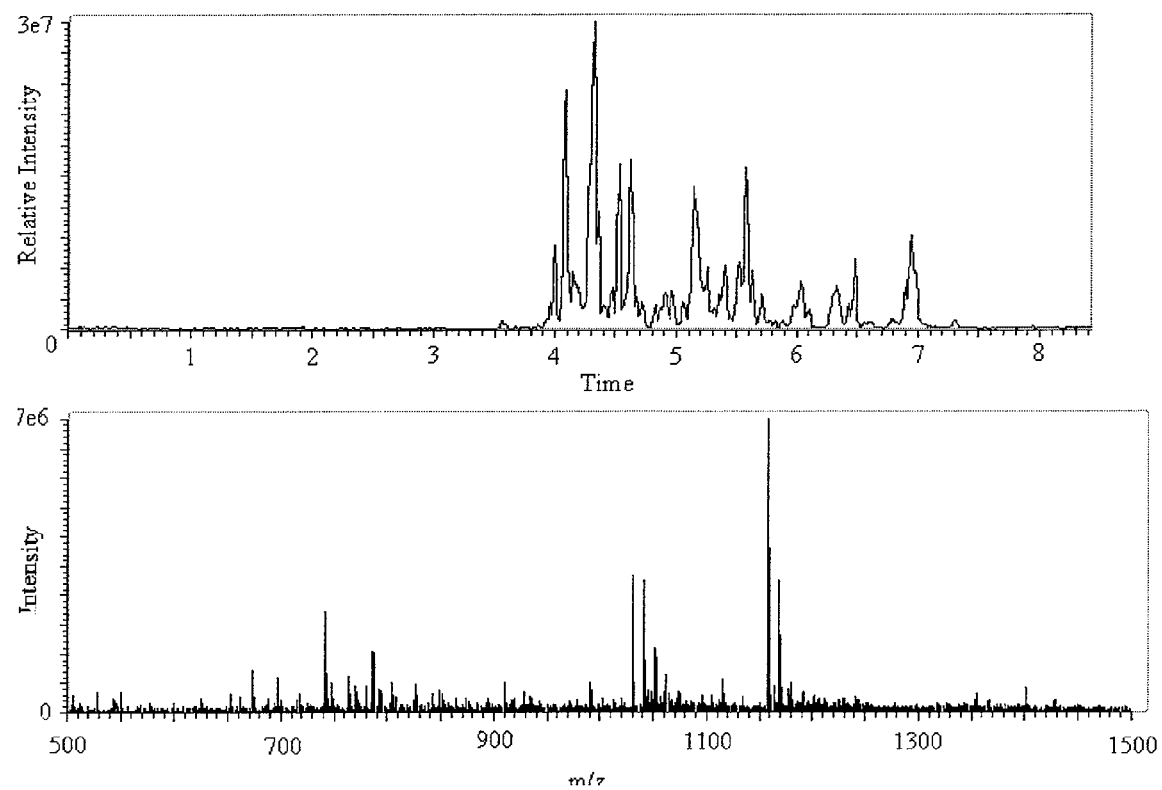
FIG. 7 is a base peak electropherogram of 6 protein digest containing: hemoglobin A (MW64,000), trypsinogen (MW 24,000), carbonic anhydrase (MW 29,000), cytochroine c (MW 12,360), α-casein (MW 23,000), and β-casein (MW 24,000) (top). Bottom graph shows the mass spectrum of the peak marked with *.

The performance of the porous tip design for the analysis of protein mixtures and digest of protein mixtures, the mixture of intact proteins, and the peptide mixture obtained from tryptic digestion of the 6-protein mixture was analyzed. FIG. 6 shows the base peak electropherogram obtained from the 5 protein mixture injection, as well as good peak separation for the known compounds, while observing minimal peak broadening. FIG. 7 shows the base peak electropherogram obtained from the tryptic digest of the 6 protein mixture. To increase throughput, a 60-cm-long capillary was used, which resulted in the analysis time of ~12 min and ~8 min for the protein mixture and the digest of the protein mixture, respectively. Almost complete baseline separation was achieved in both cases.

Figure 8:
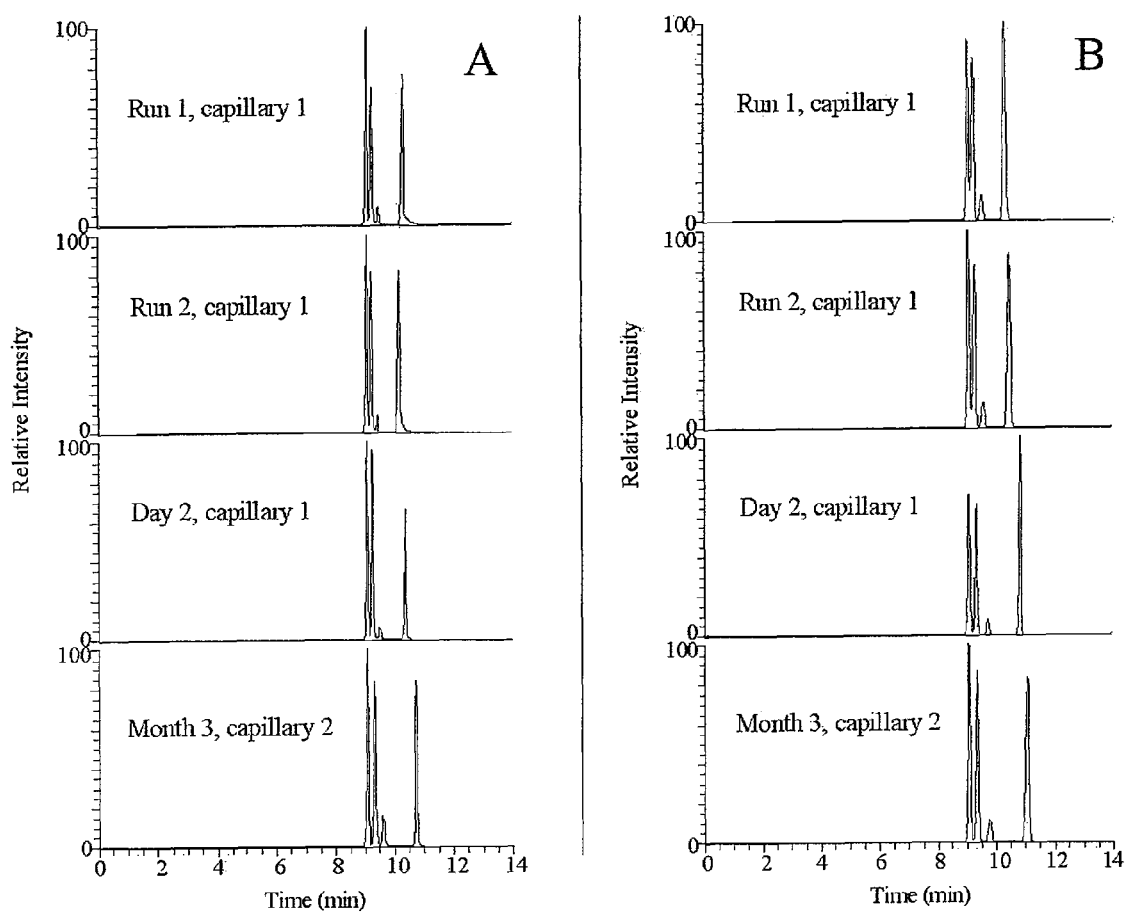
FIG. 8 is a run-to-run, day-to-day, and long-term (capillary-to-capillary) reproducibility of the analysis of the peptide standard using a BGE containing 33 nM PB (Panel A) or 33 nM PE (Panel B) and using one point calibration.
Figure 9:
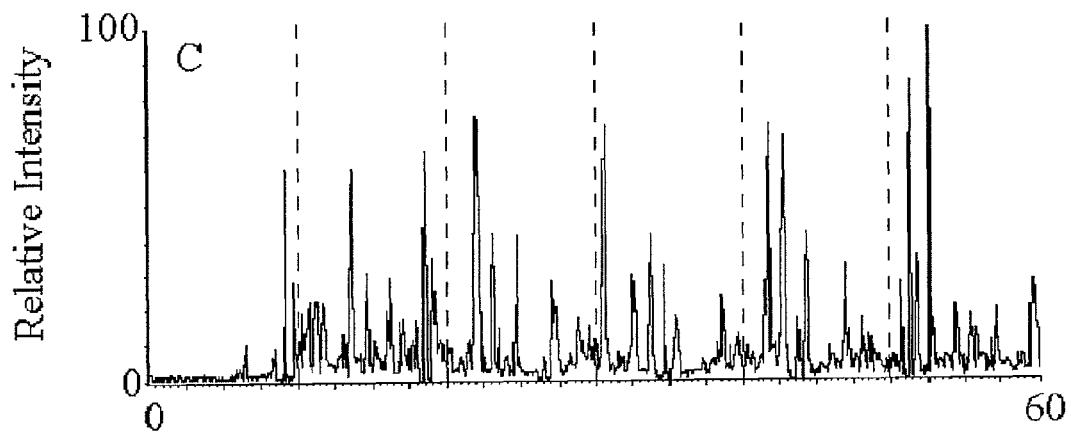
FIG. 9 is an electropherogram of a (CE-MS-MS) [6], in which the digest of a 6-protein mixture was injected every 10 min followed by CE-MS-MS analysis using dynamic exclusion.

The porous tip is very robust and may last for weeks (FIG. 8), and is reproducible. For example, FIG. 9 shows an electropherogram of a (CE-MS-MS) [6], in which the digest of a 6-protein mixture was injected every 10 min followed by CE-MS-MS analysis using dynamic exclusion. Recently (CE-MS-MS)$^n$ has been introduced for high sequence coverage proteomics [26]. The porous tip may allow for ease of interfacing CE to MS.

Application of Porous Tip to nLC-MS

To demonstrate the utility of the porous tip for interfacing higher flow separation technique such as nano-LC to MS, a 60-cm-long, 20-μm-i.d. capillary with a porous tip was connected to a nano-LC $C_{18}$ column using a Peek micro-union. Inserts of FIG. 3 show two ESI plumes at a flow rate of 250 mL/min (small plume), and a flow rate of 1 μL/min. As shown, a uniform spray was observed in both cases without any pneumatic assistance. A sharp tip, good electrical connections, and minimal bubble formation are the primary reasons for the uniformity of the electrospray plume under porous tip design. Another advantage of the porous tip is that the inlet and outlet inner diameters are the same, which reduces the chance of tip clogging, since any particulate that enters the porous tip capillary will exit from the other end of the capillary. In contrast, the use of a nano-spray interface using pulled tips can trap particulates with diameters larger than the tip opening because their tip is usually drawn to less than 10 μm-i.d. Since only the tip is sharp, tip clogging results in the loss of the spray tip and the analysis. Because the porous tip has similar o.d. and i.d. for ~1 inch, any damage to the tip may be repaired by cutting ~1 mm of the tip.

Figure 10:
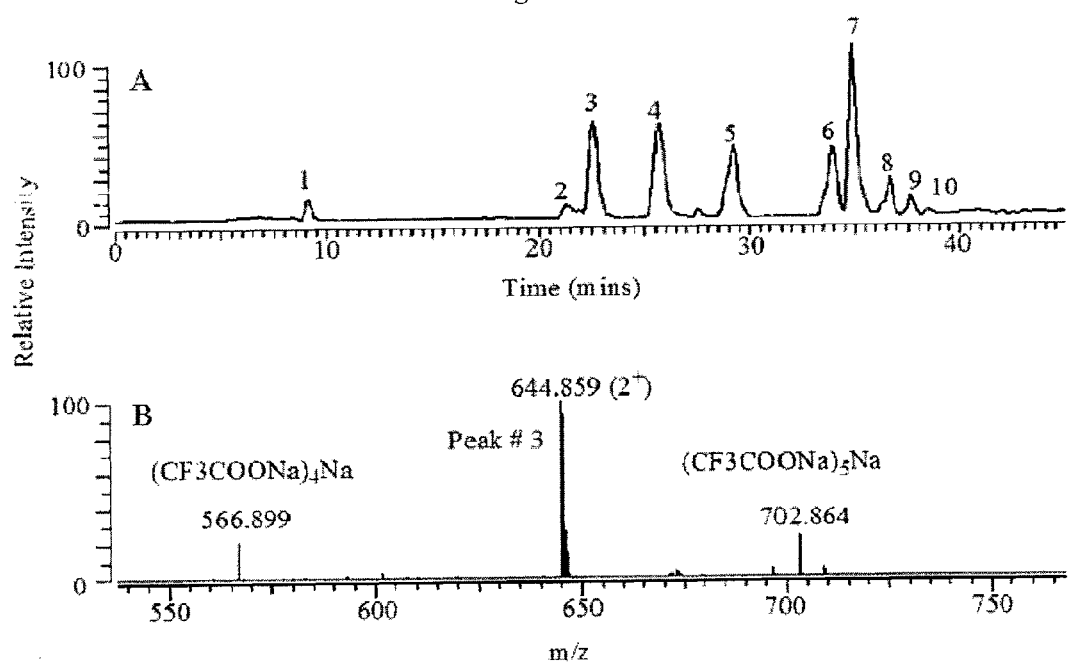
FIG. 10 (top), is a base peak nano-LC-MS chromatogram of the enolase digest using 75-μm-inner diameter (i.d.) LC column with a flow rate of 1 μm/min and (bottom) is a mass spectrum of peak #3 of the top panel.

The application of the porous tip for protein identification is demonstrated in FIG. 10, in which digested yeast enolase was analyzed using nLC in conjunction with FTICR MS. FIG. 10 shows the base peak chromatogram of the enolase digest using 75-μm-column with a flow rate of 1 μm/min. Since the dual-nozzle, dual-sprayer was used in this experiment, there were several reference peaks in every spectrum [27, 28]. These reference peaks were used for internal calibration of each spectrum resulting in a mass accuracy of less than 1 ppm in most peptide m/z. For example, FIG. 10 (bottom), shows the mass spectrum of peak #3 of FIG. 10 (top), in which the mass spectrum includes the m/z of one peptide bracketed with two reference peaks [29]. The accurate masses of the top ten intense peptide peaks are listed in Table 1 below.

TABLE 1

Measured vs. calculated masses for peaks of FIG. 3.

| Peak # | m/z Measured | MH+ Calculated | Delta ppm |
|---|---|---|---|
| 1 | 814.5040 | 814.5038 | 0.21 |
| 2 | 1159.6120 | 1159.6111 | 0.74 |
| 3 | 1286.7120 | 1286.7109 | 0.88 |
| 4 | 1288.7110 | 1288.7113 | −0.20 |
| 5 | 1412.8240 | 1412.8225 | 1.0 |
| 6 | 1416.7220 | 1416.7222 | −0.15 |
| 7 | 1578.8030 | 1578.8015 | 0.93 |
| 8 | 1755.9470 | 1755.9493 | −1.3 |
| 9 | 1840.9250 | 1840.9227 | 1.2 |
| 10 | 1872.9680 | 1872.9682 | −0.11 |

Background Electrolyte-BGE

To simplify CE-MS operation, a BGE containing a polymer additive may be introduced that allows the analysis of peptides and protein mixtures in underivatized fused-silica capillaries without any pretreatment, thereby increasing throughput. Examples of suitable BGEs include Polybrene (PB) and PolyE (PE).

Polybrene (PB) and PolyE 323 (PE) are cationic polymers that are able to non-covalently attach to the negatively charged wall of fused-silica capillary. The excess positive charges on the newly created surface generate a stable anodic EOF that is independent of pH within the pH range of 4-8. The molecular structure of both PB and PE are shown in FIG. 11. The structure of PE is purposely constructed to contain mixed bonding characteristics. For example, the nitrogen atoms in the backbone of PE are separated by three atoms length whereas nitrogen atoms in PB are separated by six carbon atoms. The length of the spacer arm between the nitrogen atoms in the backbone can affect the polymer's flexibility, and hydrophobicity. Also, hydroxyl groups in PE increase polymer immobilization on the capillary wall by hydrogen-bonding [30-32]. PB and PE are very effective in reversing the charge on the capillary wall, which prevents peptide and protein attachment to the capillary wall, thereby significantly improving separation efficiency (FIG. 12). To be useful in CE/ESI-MS, the suppression effect of the additive reagent on analytes of interest must be insignificant. PE and PB have such characteristics, i.e., they do not produce significant background signal (FIG. 13) and do not significantly suppress the signals of the proteins and peptides under electrospray ionization (FIG. 14), thereby allowing them to be used as an additive to common BGEs that are used for CE-MS analysis of peptide and protein mixtures. In addition, because the fused-silica capillary inner wall is continuously coated with the polymer additive, migration irreproducibility, due to the degradation of the capillary inner wall coating, under CE-MS is minimized. High sensitivity of detection, migration reproducibility, and ease of fabrication allow CE-MS analyses that require long analysis time, such as (CE-MS/MS)n, to be performed with ease. Recently we have shown the utility of these background electrolytes for the analysis of complex protein digests and intact proteins [32].

Polybrene was purchased from Sigma Chemical Co. (St. Louis, Mo.). PolyE 323 polymer was prepared according to a reported procedure [30]. Briefly, a stock solution of PolyE 323 polymer was synthesized by combining 0.1 mol of 1,2-bis(3-aminopropylamino)ethane with 20 mL of water and 0.1 mol of epichlorohydrine. This mixture was then stirred for 48 h, after which an additional 100 mL of water was added before storage at 8° C. without further purification. A stock solution of polybrene (hexadimethrine bromide, average MW=15,000) was made by mixing 5 mg of polybrene in 100 mL of HPLC grade water (3.3_M). Aliquots of this solution were diluted with 0.1% acetic acid to final concentrations of 33, 66, 330, and 660 nM.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

REFERENCES

1. Luo, Q.; Shen, Y.; Hixson, K. K.; Zhao, R.; Yang, F.; Moore, R. J.; Mottaz, H. M.; Smith, R. D.; Anal. Chem. 2005, 77, 5028-5035.
2. Whitt, J. T.; Moini, M.; Anal. Chem. 2003, 75, 2188-2191.
3. Moini, M. Anal. Bioanal. Chem. 2002, 373, 466-480.
4. Clinical and Forensic Applications of Capillary Electrophoresis; Pertsen, J. R.; Mobamm.ad, A. D., Ed.; Humana Press: Totowa, N.J., 2001.
5. Brocke, A. V.; Nicholson, G.; Bayer, E. Electrophdresis 2001, 22, 1251-1266.
6. Severs, J. C.; Smith, R. D. In Electrospray Ionization Mass Spectrometiy•Electrophoresis-Electrospray Ionization Mass Spectrometry: Cole, R. B., Ed.; John Wiley: New York, 1997.
7. Dovichi, N.J.; Krylov, S. N. Anal. Chem. 2002, 72, 111-128.
8. Ding, J. M.; Vouros, P. Anal. Chem. 1999, 71, 378A-385A.
9. Cai, J.; Henion, J of Chrom. 1995, 703, 667-692.
10. Aebersold, R.; Figeys, D. Electrophoresis 1998, 19, 885-892.
11. Preisler, J.; Hu, P.; Rejtar, T.; Karger, B. L. Anal. Chem. 2000, 72, 4785-4795.
12. Moini, M. Anal. Chem. 2001, 73, 3497-3501.
13. Figeys, D.; Ducret, A.; Aebersold, R. J. Chromatography A, 1997, 763, 295-306.
14. Janini, G. M.; Conrad, T. P.; Wilkens, K. L.; Issaq, H. J., and Veenstra, T. D.; Anal.Chem 2003, 75, 1615-1619
15. Settpage, E. R.; Russo, P. S.; Shabanowitz, J.; Hunt, D. F.; J. Microcolumn September 1988, 10, 281-285
16. Yeung, E. S.; Wei, W. Anal Chem. 2002, 74, 3899-3905.
17. Quirino, J. P.: Dulay, M. T.; Bennet, B. D.; Zare, R. N. Anal. Chem. 2001, 73, 5539-5543.
18. Quirino, J. P.: Dulay, M. T.; Zare, R. N. Anal. Chem. 2001, 73, 5557-5563.
19. Khandurina, J.; Jacobson, S. C.; Waters, L. C.; Foote, R. S.; Ramsey, J. M. Anal. Chem. 1999, 71, 1815-1819.
20. Guzman, N. A.; Stubbs, R. J. Electrophoresis 2001, 22, 3602-3628.
21. Wei, W.; Xue, G.; Yeung, E. S. Anal. Chem. 2002, 74, 934-940.

22 Moini, M. *Anal Chem* 2007, 79, 4241-4246
23. "Moini, M. "Capillary Electrophoresis/Electrospray Ionization Mass Spectrometry of Amino Acids, Peptides, and Proteins" in "Capillary Electrophoresis of Peptides and Proteins", Methods in Molecular Biology, Volume 276, Ch. 13, p 253-290, Humana Press, 2004, Editors: Strege, M. A., and Lagu, A. L.
24. Takada, Y.; Nakayama, K.; Yoshida, M.; Sakairi, M. *Rapid Commun. Mass Spectroin.* 1994, 8, 695.
25. Moini, M.; Schultz, C. L.; Mahmood, H.; Anal. Chem. 2003, 75, 6282-6287
26. Garza, S.; Moini, M. *Anal. Chem.* 2006, 78, 7309-7316.
27. Jiang, L.; Moini, M. *Anal. Chem.* 2000, 72, 20; and *Anal. Chem.* 2000, 72, 885.
28. "Mass Spectrometer with Multiple Atmospheric Pressure Inlets (Nozzles)", Longfei Jiang and Mehdi Moini, University of Texas at Austin. U.S. Pat. No. 6,465,776 1B, Issue Date Oct. 15, 2002.
29. Moini, M.; Jones, B. L.; Rogers, R. M.; Jiang, L. *J. Am. Soc. Mass Spectrom.* 1998, 9, 977.
30. M. X. Li, L. Liu, J. Wu, D. M. Lubman, Anal. Chem. 69 (1997) 2451.
31. S. Ullsten, A. Zuberovic, M. Wetterhall, E. Hardenborg, K. E. Markides, J. Bergquist, Electrophoresis 25 (2004) 2090.
32. Selynda Garza, Silvia Chang, Mehdi Moini, Journal of Chromatography A, 1159 (2007)14-21.

What is claimed is:

1. A method comprising:
providing a capillary column comprising a terminus and an exterior surface; and
creating a plurality of pores in the exterior surface of the capillary column to form a porous segment at the terminus of the capillary column.

2. The method of claim 1, wherein at least a portion of the exterior surface comprises a coating, and further comprising removing at least a portion of the coating prior to creating the plurality of pores in the exterior surface.

3. The method of claim 2, wherein removing at least a portion of the coating on the exterior surface comprises exposing at least a portion of the exterior surface to a solution of acid or heat.

4. The method of claim 2, wherein the coating comprises polyimide.

5. The method of claim 1, wherein creating a plurality of pores in the exterior surface comprises exposing the exterior surface to at least one selected from the group consisting of a solution of acid, a solution of base, and a mechanical tool.

6. A capillary column comprising:
a terminus and an exterior surface, wherein the exterior surface at the terminus of the capillary column comprises a plurality of pores so as to form a porous segment.

7. The capillary column of claim 6, wherein at least a portion of the exterior surface comprises a polymer coating.

8. The capillary column of claim 7, wherein the portion of the exterior surface that comprises a polymer coating is not at the terminus.

9. The capillary column of claim 6, further comprising a conductive solution.

10. The capillary column of claim 6, further comprising a conductive solution, wherein the conductive solution comprises one or more cationic polymers.

11. The capillary column of claim 6, further comprising a conductive solution, wherein the conductive solution comprises polybrene or polyE 323 or both.

12. A system comprising:
a capillary column comprising a terminus and an exterior surface, wherein the exterior surface at the terminus of the capillary column comprises a plurality of pores so as to form a porous segment; and
one or more instruments selected from the group consisting of an electrophoresis instrument, a high performance liquid chromatography instrument, and a mass spectrometry instrument, wherein the porous segment serves as an interface between the capillary column and the instrument.

13. The system of claim 12, wherein the capillary column further comprises a conductive solution.

14. The system of claim 12, wherein the instrument is an electrophoresis instrument.

15. The system of claim 12, wherein the instrument is a high performance liquid chromatography instrument.

16. The system of claim 12, wherein the instrument is a mass spectrometry instrument.

17. A method comprising:
providing a capillary column comprising a terminus and an exterior surface, wherein the exterior surface at the terminus of the capillary column comprises a plurality of pores so as to form a porous segment;
providing a mass spectrometer in operable relation to the capillary column;
interfacing the mass spectrometer with at least a portion of the porous segment at the terminus of the capillary column;
injecting a mixture containing a chemical or biological sample into the capillary column;
transporting at least a portion of the mixture to the mass spectrometer; and
analyzing the portion with the mass spectrometer to identify the composition of the chemical or biological sample in the portion.

18. The method of claim 17, further comprising:
preconditioning the capillary column with a buffer solution prior to injecting the mixture.

19. The method of claim 17, further comprising:
providing a metal sheath;
inserting the capillary column comprising the porous segment into the metal sheath or a container containing conductive solution to which voltage is applied prior to interfacing the mass spectrometer with at least a portion of the porous segment; and
filling the metal sheath with a conductive solution.

20. A method comprising:
providing a capillary electrophoresis eluent disposed within a capillary column comprising a terminus and an exterior surface, wherein the exterior surface at the terminus of the capillary column comprises a plurality of pores so as to form a porous segment;
grounding the capillary column through at least a portion of the porous segment; and
depositing the capillary electrophoresis eluent onto a Matrix Assisted Laser Desorption Ionization plate.

* * * * *